US006918534B2

(12) United States Patent
Fitzgibbons et al.

(10) Patent No.: US 6,918,534 B2
(45) Date of Patent: Jul. 19, 2005

(54) COLLECTION BOX WITH SEALED AND STATICALLY CHARGED MAIL CHUTE

(75) Inventors: Patrick J. Fitzgibbons, Owego, NY (US); Christopher J. Tatar, Endicott, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 27 days.

(21) Appl. No.: 10/411,904

(22) Filed: Apr. 11, 2003

(65) Prior Publication Data

US 2003/0192946 A1 Oct. 16, 2003

Related U.S. Application Data

(60) Provisional application No. 60/372,467, filed on Apr. 12, 2002.

(51) Int. Cl.$^7$ ............................................. B65G 11/04
(52) U.S. Cl. ............................. 232/50; 232/45; 193/8
(58) Field of Search ........................... 232/44, 51, 52, 232/45, 47, 49, 50; 193/8, 17; 312/124

(56) References Cited

U.S. PATENT DOCUMENTS

| 560,477 | A | * | 5/1896 | Cook | ..................... 232/50 |
|---|---|---|---|---|---|
| 3,254,215 | A | | 5/1966 | Oliphant | |
| 3,935,517 | A | | 1/1976 | O'Brien | |
| 4,363,438 | A | | 12/1982 | Connor | |
| 6,199,244 | B1 | | 3/2001 | Hilgers et al. | |
| 6,299,061 | B1 | | 10/2001 | Henson | |
| 6,359,246 | B1 | * | 3/2002 | Essig et al. | .............. 209/127.1 |
| 6,399,157 | B1 | | 6/2002 | Zaretsky | |

OTHER PUBLICATIONS

Brown, S. C. *Basic Data of Plasma Physics* (1961). Cambridge, MA: MIT Press, pp. 268–274.
Triboelectric Series at http://www.amasci.com/emotor/tribo.txt. Retrieved Apr. 10, 2003.
U.S. Appl. No. 60/372,467, filed Apr. 12, 2002. Title: Collection Box with Sealed and Statically Charged Mail Chute. Applicants: Patrick J. Fitzgibbons et al.

* cited by examiner

*Primary Examiner*—William L. Miller
(74) *Attorney, Agent, or Firm*—Perkins Smith & Cohen LLP; Orlando Lopez; Peter J. Borghetti (57) ABSTRACT

A system and method for substantially eliminating the release of pathogen agents circulating in the air within a collection box. The mail deposit openings (12, 14) of a collection box mail chute (16) are adapted with gaskets (18, 20) to form an airtight seal when the mail chute (16) is opened and closed, thereby isolating the collection box interior (26). An alternative embodiment can further include a charging device (32) and a chargeable material (34) to attract and detain airborne and free pathogen particles that enter the mail chute passage (22) either by newly deposited mail pieces (38) or airborne pathogen particles that migrated from within the collection box collection area (26).

35 Claims, 8 Drawing Sheets

COLLECTION BOX WITH SEALED AND STATICALLY CHARGED MAIL CHUTE

CROSS REFERENCE TO RELATED APPLICATIONS

This application claims priority of U.S. Provisional Application No. 60/372,467 filed on Apr. 12, 2002, which is herein incorporated by reference.

BACKGROUND OF THE INVENTION

This invention relates generally to the containment of hazardous material in an enclosure, and, more particularly to the attraction and detainment of pathogen agents disposed in or on mail pieces or airborne pathogen particles in a collection box.

The possibility of using postal services or delivery services to release pathogen agents has been demonstrated. Unsuspecting recipients can be harmed by the release of such pathogen agents. Equally at risk are those handling the mail pieces or the packages to be delivered. There appears to be no current security devices or procedures that are available to intercept such mail pieces at the earliest source of introduction into the delivery system, for example at the collection box or post office drop box.

Mail collection boxes commonly found on street corners pose a potential risk to mail carriers and customers. Once a single contaminated mail piece enters the collection box, all mail pieces deposited can be exposed to particles of contamination that have been released from the mail piece into the surrounding air. Thereby, mail carriers can be exposed to airborne pathogen particles when they perform their duties of picking up the mail. Therefore, it is desirable to reduce or preferably capture and retain airborne particles of pathogen agents from collection box atmosphere including the mail tub and chamber.

Additionally, airborne pathogen particles pose a risk to customers each time they open a mail slot of the mailbox to deposit mail. The opening and closing of the mail slot causes air to circulate within the collection box. Air circulation could agitate the pathogen agents laying dormant in the mail tub or affixed to the walls, floor, or other internal components of a collection box and agitate these airborne particles already in the collection box atmosphere. The dormant pathogen particles may become loose and float freely in the air circulating within the collection box and migrate to the collection box mail chute, thereafter pathogen agents can be released into the outside environment in the presence of the customer. Therefore, it is desirable to substantially eliminate the release of pathogen agents circulating in the air within a collection box through the collection box chute to the outside atmosphere.

SUMMARY OF THE INVENTION

In one embodiment of the invention, the mail deposit opening(s) of a collection box mail chute are adapted with gaskets to form an airtight seal when the mail chute is opened and closed, thereby isolating the collection box interior and contents from outside atmosphere. The gaskets are made of material with good elastic and compressive properties and conventionally attached to the mail chute.

Additionally, a further embodiment of the invention provides the collection box mail chute with charging means and statically chargeable material(s) to attract and detain airborne pathogen particles prior to mail pieces being dropped into the collection box interior. The charging means are operatively connected to a mail inlet cover of the collection box, such that when the inlet cover is closed or opened the charging means are activated. The charge generated by the charging means is used to statically charge the surface of a chargeable material. In one embodiment, the charging means include triboelectric charging means. In another embodiment, the charging means include a voltage source and electrodes. Pathogen agents contain opposite charged particles that are drawn to the statically charged surface of the chargeable material for appropriate disposal. The collection box is grounded to assure mail carriers and customers are not shocked while dropping off mail or performing duties of retrieving the mail.

For a better understanding of the present invention, together with other and further objects thereof, reference is made to the accompanying drawings and detailed description and its scope will be pointed out in the appended claims.

DETAILED DESCRIPTION OF THE PREFERRED EMBODIMENTS

A system and method for substantially eliminating the release of pathogen agents circulating in the air within a collection box is described herein below.

Figure 1:
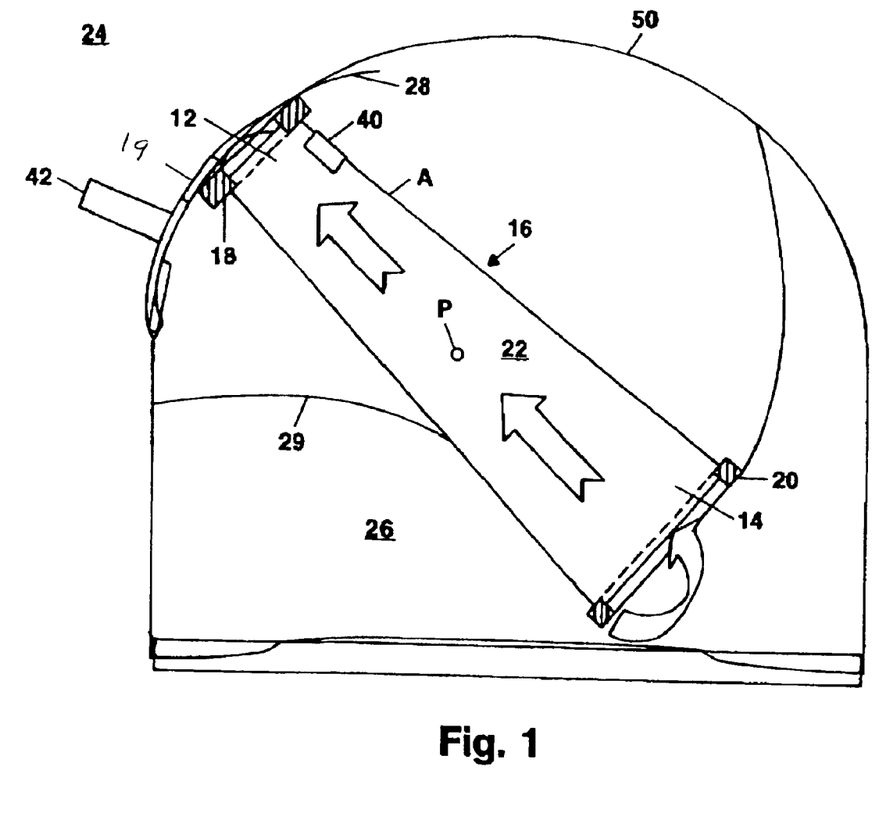
FIG. 1 is a sectional side view of an embodiment of a collection box of the present invention.
Figure 2:
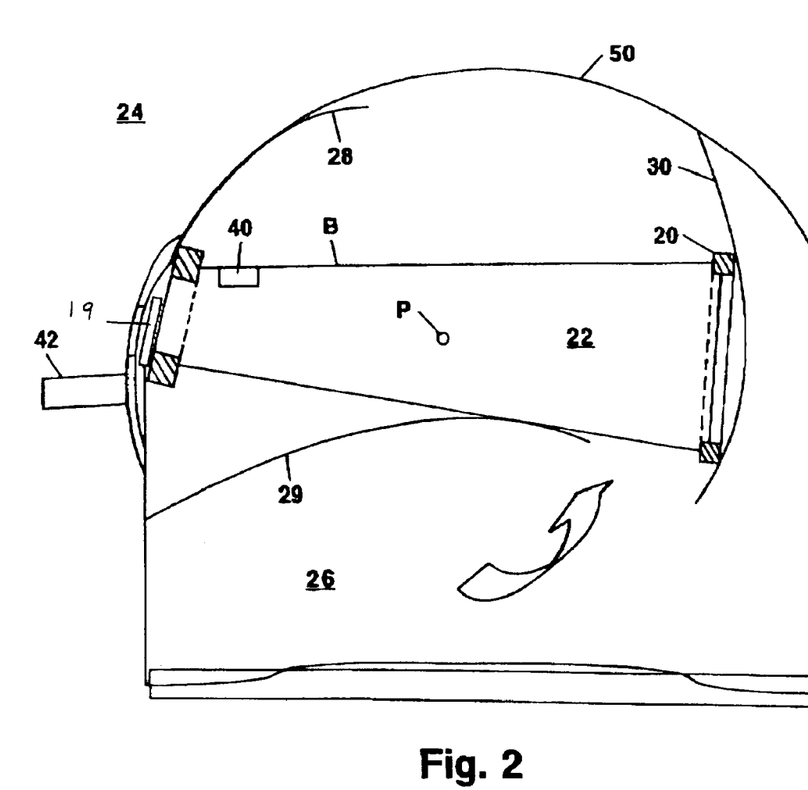
FIG. 2 is a sectional side view of the above embodiment of the present invention shown in the operational configuration capable of receiving mail.

Referring to FIGS. 1 and 2, inlet mail deposit opening 12 and outlet mail deposit opening 14 of a rotating collection box mail chute 16 are adapted with inlet 18 and outlet 20 gaskets to form a seal when the mail chute 16 is opened and/or closed, thereby isolating the collection box collection area 26 and contents from the outside atmosphere 24. Airflow is restricted from migrating out of the mail chute 16 either into the outside environment 24 or into the collection box collection area 26.

In the closed position A, as illustrated in FIG. 1, the collection box internal air can migrate about the mail chute passage 22 due to air circulation caused by inherent leaks from seams, bolts and rivets of the collection box and by the fanning effect generated by the mail chute 16 being opened and closed. It is possible that pathogen particles deposited in or on mail pieces or pathogen particles that have settled on surfaces of the collection box collection area 26 will become airborne as a result of the drafts, fanning and turbulence and migrate into the mail chute passage 22. However, the airborne pathogen particles cannot leak out of the mail chute passage 22 because inlet gasket 18 seals the leakage path between the mail chute 16, a front transition liner 28, and a mid transition liner 29 or the like.

In the open position B, as illustrated in FIG. 2, the collection box internal air cannot migrate into the mail chute passage 22 because outlet gasket 20 seals the leakage path between the mail chute 16 and an aft transition liner 30, and a mid transition liner 29 or the like.

The gaskets 18, 20 are made of conventional gasket material with good elastic and compressive properties and conventionally attached to the mail chute 16 adjacent respective openings 12, 14. As shown in FIG. 2, openings 12 align with opening 19 in collection box 50.

Referring again to FIGS. 1 and 2, the method for isolating mail items in the collection box of this invention can be described as follows. The mail chute 16 is pivotally mounted within the collection box thereby allowing for rotational movement. By rotating the mail chute 16, the input end (inlet mail deposit opening) 12 of the mail chute 16 is substantially aligned with the opening 19 in the collection box 50. In one embodiment of the present invention, the mail chute 16 is operably connected to means for covering the opening 19 in the collection box 50, such as the mail inlet cover 42. In the embodiment in which the mail chute 16 is operably connected to the mail inlet cover 42, when the cover 42 is opened, the mail chute 16 is rotated so that the input end 12 of the mail chute 16 aligned with the opening 19, thereby being able to receive mail items through the input end 12 from the opening 19 (see FIG. 1). When the mail chute 16 is rotated so that the input end 12 of the mail chute 16 aligned with the opening 19, the output end (outlet mail deposit opening) 14 of the mail chute 16 is substantially sealed due to the contact between the sealing gaskets 20 and the aft transition liner 30, thereby isolating the exterior 24 of the collection box 50 from the mail items previously collected and deposited in the collection area 26.

In the embodiment in which the mail chute 16 is operably connected to the mail inlet cover 42, when the cover 42 is closed, the mail chute 16 is rotated so that the input end 12 of the mail chute 16 moves away from the opening 19 and the output end 14 moves to a position that enables mail to be deposited from the mail chute passage 22 to the collection area 26. As the is rotated so that the input end 12 of the mail chute 16 moves away from the opening 19, the input end 12 is sealed due to the contact between the sealing gaskets 18 and the front transition liner 28 (see FIG. 2). Due to the rotation that moves the input end 12 away from the opening 19, the output end 14 is unsealed since the outlet gasket 20 is moved away from being in complete contact with the aft transition liner 30. As shown in FIG. 2, the mail items can be deposited in the collection area 26. Again, the exterior 24 of the collection box 50 from the mail items previously collected and deposited in the collection area 26. It should be noted that, as the input end 19 moves from the position shown in FIG. 2 to the position in which the input end 12 is aligned with the opening 19, as shown in FIG. 1, the input end 12 goes from a sealed condition to an unsealed condition.

Figure 3:
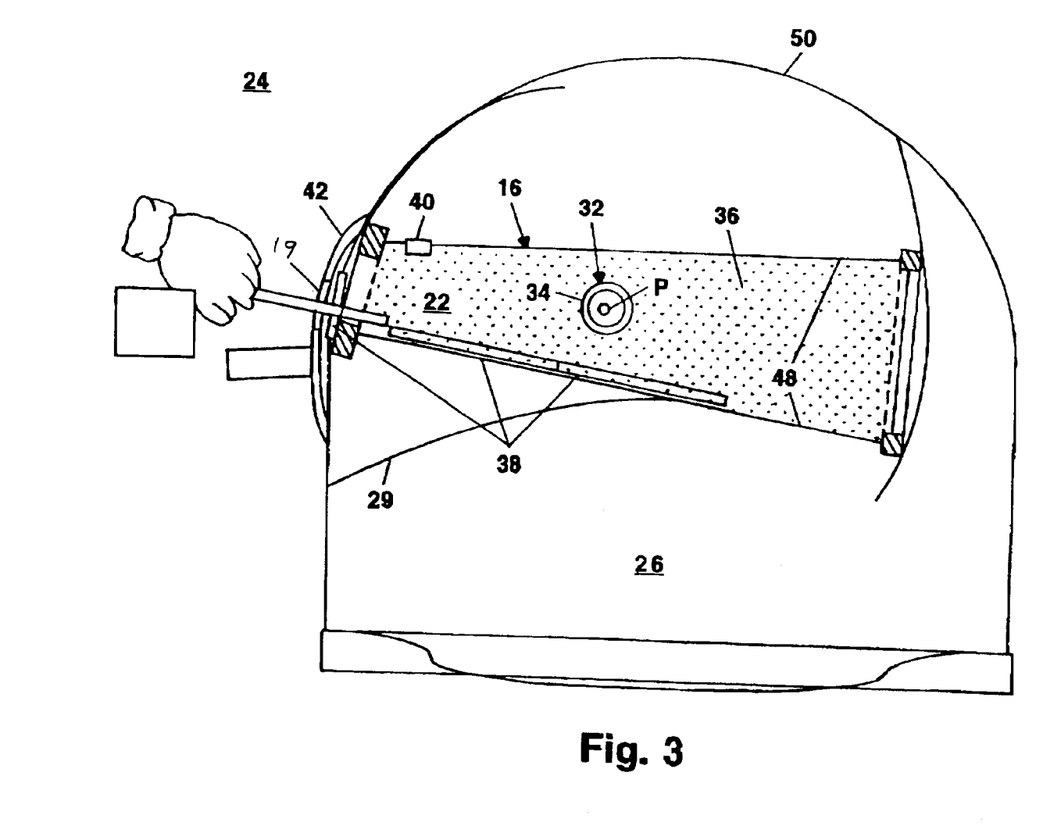
FIG. 3 is a sectional side view of another embodiment of the present invention.
Figure 4A:
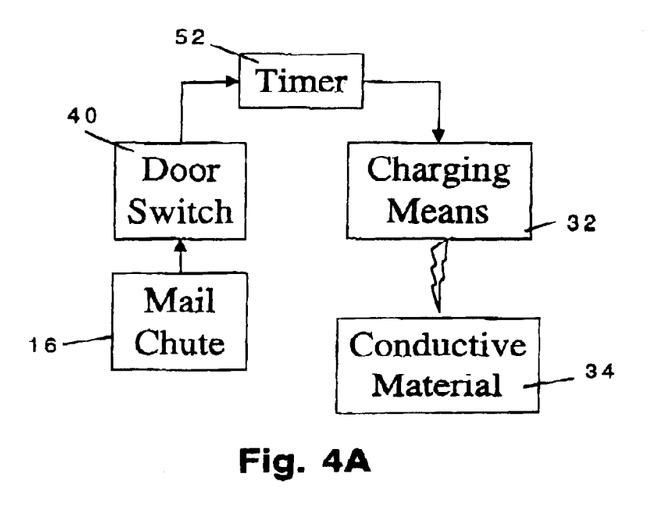
FIG. 4a is a block diagram of an electrical sub-system of one embodiment of the present invention.
Figure 4B:
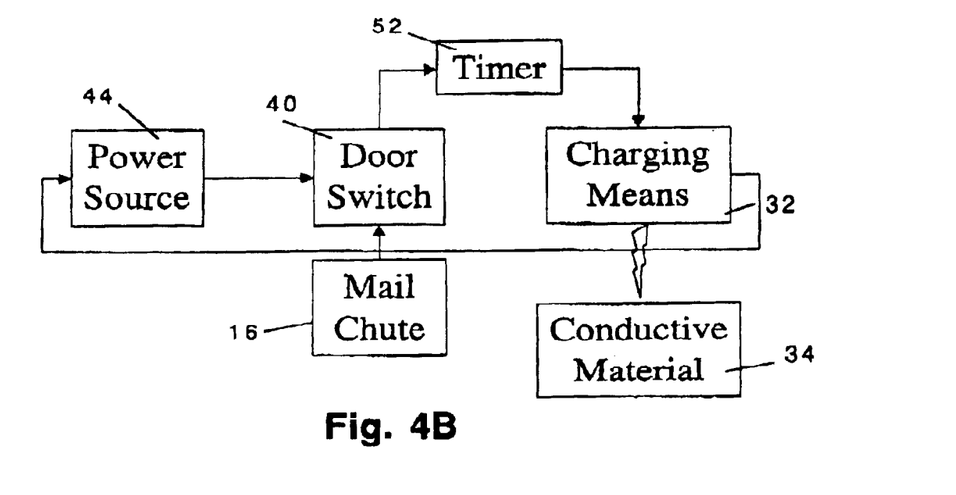
FIG. 4b is another block diagram of the electrical sub-system of one embodiment of the present invention.

Now turning to FIG. 3, another embodiment of the present invention can further include electrical charging means 32 and a statically chargeable material 34 to attract and detain airborne pathogen particles 36 that enter the mail chute passage 22 either by newly deposited mail pieces 38 or airborne pathogen particles that migrated from within the collection box collection area 26, as discussed above. As illustrated in FIGS. 4a and 4b, electrical charging means 32 are operatively connected to a door switch 40 preferably attached to the mail chute 16 (shown in FIGS. 1 and 2). In another embodiment, the electrical charging means 32 are mechanically operably connected to the mail chute 16. In the embodiment in which the electrical charging means 32 are mechanically operably connected to the mail chute 16, operation of the mail chute 16 causes operation of the charging means 32. Electrical charging means can be contact charging mechanisms or can include a static generator and a power source. In the embodiment including the static generator, the static generator is powered by a power source 44 (shown in FIG. 4*b*). Power source 44 is a power source such as, but not limited to, a DC source such as a battery, an AC source and a power supply, an AC source or a solar powered (photo-voltaic) DC source.

Referring again to FIG. 3, it should be noted that embodiments of the present invention including a mail chute 16 with charging means 32, whether the mail chute 16 is moveable or non-moveable and whether the mail chute 16 is sealable or non-sealable, are within the scope of this invention. Although an internal chute 16 is shown in FIG. 3, an embodiment with an external chute is also within the scope of the present invention. If the chute 16 is external to the collection box 50, the output end is aligned with the opening 19 in order to allow passage of mail items into the collection area 26. If the chute 16 is internal to the collection box 50,as shown in FIG. 3, the input end is aligned with the opening 19 in order to allow passage of mail items into the collection area 26. The charging means 32, in one embodiment, are operably connected to the mail inlet cover 42. The operable connection between the mail inlet cover 42 and the charging means can be electrical, as via the door switch 40, or mechanical.

The door switch 40 can be physically positioned at any location and in any conventional manner to the static or rotating components of the collection box 50. The key factor in determining location is whether to activate the static generator (charging means) 32 when the mail chute 16 is opened or closed. Embodiments of the door switch 40 may include a toggle-like switch positioned on the static components of the collection box 50, such as the front transition liner 28, aft transition liner 30, or collection box 50. Other embodiments may include a limit switch 40 positioned on the rotating components of the collection box 50, such as the mail chute 16 to sense angular change. In any of the above-mentioned door switch embodiments, the rotation of the mail chute 16 will activate and deactivate the charging means 32. However, the preferred location is at the inlet mail deposit opening 12 mounted to the mail chute interior walls 48, as illustrated in FIGS. 1–3. The charging means 32 can be activated when the mail chute 16 is rotated to a predetermined angle. The charging means 32 can be deactivated when the mail chute 16 returns to its resting position or, preferably, after a predetermined time.

FIGS. 5*a*, 5*b* depict embodiments in which the charging means 32 include contact charging mechanisms. Referring to FIG. 5*a*, the materials comprising sector section 62 and 64 are selected from opposite ends of the triboelectric series. For example, the material of negative polarity, such as a slightly conductive polymer, is used in sector section 64 and the material of positive polarity, such as nylon or glass, is used in sector section 62. The material of negative polarity should have sufficient retention properties including high surface resistivity, such as $10^{15}$ Ohms @ 20° C. and 50% humidity, that reduces leakage and allows for retention of voltage or charge, and a low dielectric constant that allows for high surface charge. The sector section 62 and 64 are brought in contact and not grounded. (The sector section 62 and 64 could be brought into contact by a spring action initiated upon activation.) When the mail chute 16 is rotated to a predetermined angle, the sector section 62 and 64 are no longer in contact or oppositely disposed and become charged. When the mail chute 16 returns to its resting position or, preferably, after a predetermined time, sector section 62 and 64 return back to the position shown in FIG. 5a and the charging means 32 can be deactivated by grounding the sector section 62 and 64 with grounding element 70.

Figure 5A:
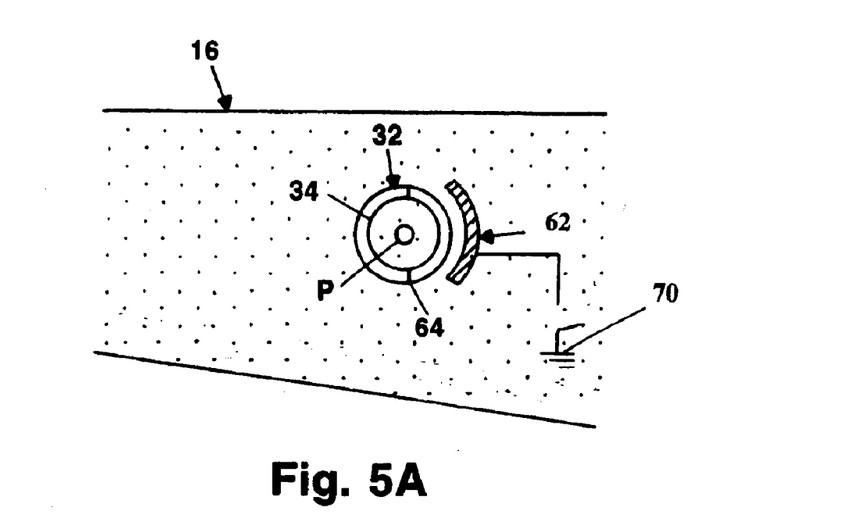
FIG. 5a is a sectional side view of a portion of another embodiment of the present invention illustrating one embodiment of the activation of charging means.
Figure 5B:
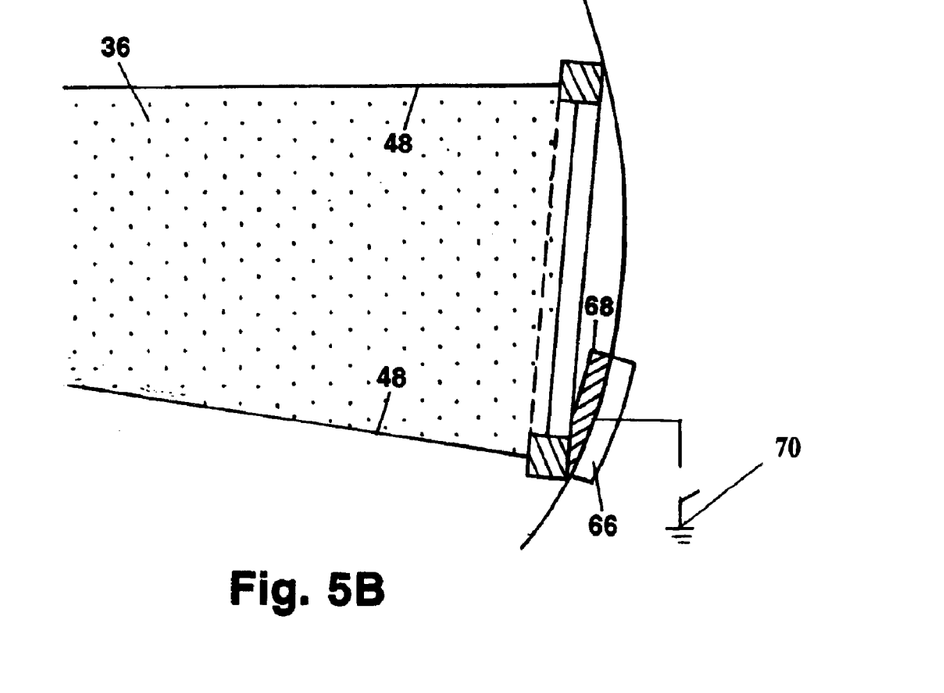
FIG. 5b is a sectional side view of a portion of another embodiment of the present invention illustrating another embodiment of the activation of charging means.

Another embodiment in which the charging means 32 include contact charging mechanisms is shown in FIG. 5b. Referring to FIG. 5b, the materials comprising sector section 66 and 68 are selected from opposite ends of the triboelectric series. For example, the material of negative polarity is used in sector section 68 and the material of positive polarity is used in sector section 66. The material of negative polarity should have sufficient retention properties including high surface resistivity, such as $10^{15}$ Ohms @ 20° C. and 50% humidity, that reduces leakage and allows for retention of voltage or charge, and a low dielectric constant that allows for high surface charge. The sector section 66 and 68 are brought in contact and not grounded. (The sector section 62 and 64 could be brought into contact by a spring or solenoid action initiated upon activation.) When the mail chute 16 is rotated to a predetermined angle, the sector section 66 and 68 are no longer in contact or oppositely disposed and become charged. When the mail chute 16 returns to its resting position or, preferably, after a predetermined time, sector section 66 and 68 return back to the position shown in FIG. 5b and the charging means 32 can be deactivated by grounding the sector section 66 and 68 with grounding element 70.

Figure 5C:
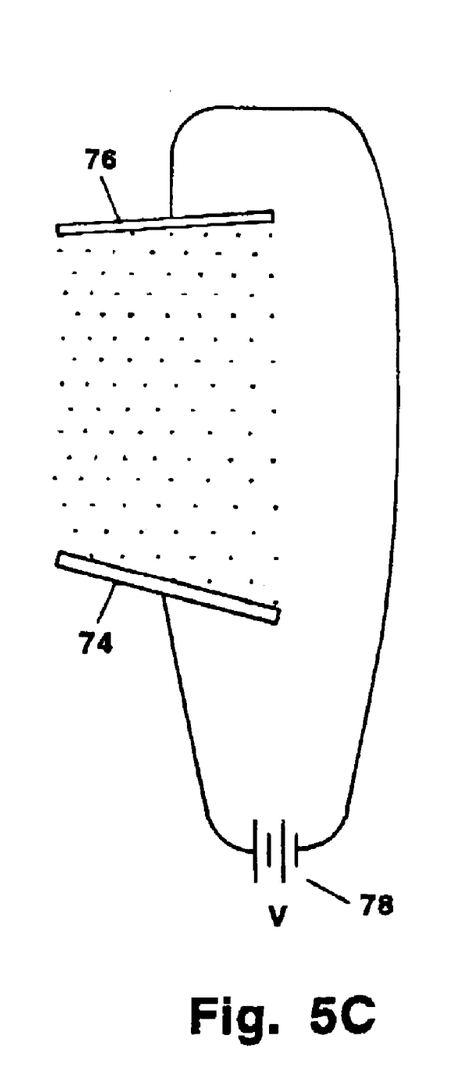
FIG. 5c is a sectional side view of a portion of another embodiment of the present invention illustrating yet another embodiment of the activation of charging means.

A further embodiment of charging means 32, shown in FIG. 5c, include electrodes 74, 76 and the voltage source 78. Referring to FIG. 5c, electrodes 74 and 76 when connected to voltage source 78 produce an electric field substantially perpendicular to the surface of the electrodes 74 and 76. Electrodes 74, 76 have sufficient surface area to effectively collect charged pathogens. The material used for electrodes 74, 76 include conductive materials and dielectrics with a conductive backing. The voltage 78 and distance between the electrodes 74 and 76 (or the geometry of the electrodes) is selected so that the biological agents are held by the electric field but such that avalanche breakdown of the ambient gas does not occur. Such designs are known in the art (see, for example, S. C. Brown, *Basic Data of Plasma Physics*, M.I.T. Press, Cambridge, Mass., 1961, pp. 268–274). The actual voltage required is determined by the shape of the electrode, the distance between electrodes, the composition (elements and density) of the ambient gas.

It should be noted that other embodiments of the charging means could be used, For example, a system similar to that of U.S. Pat. No. 3,935,517 (issued to J. F. O'Brien on Jan. 27, 1976) could be used. The device of patent '517 has to be adapted to the conditions of non constant speed of the chargeable material 34. The chargeable material 34 would include, in this embodiment, a dielectric with a conductive backing. The speed of the chargeable material 34, in this embodiment, is not constant since the chargeable material 34 moves past the charging roller (the charging roller being as described in '317) as the mail chute 16 is rotated.

In yet another embodiment of the charging means (not shown), a corona charging system is utilized to charge the chargeable material 34. The chargeable material 34 would include, in this embodiment, a dielectric with a conductive backing. The corona charging system includes a corona electrode, another electrode that incorporates the chargeable material 34 and voltage source 44. Corona charging of dielectrics has been used in xerography and is also in web coating technology (see, for example, U.S. Pat. No. 3,254,215 to K. M. Oliphant issued on May 31, 1966 and U.S. Pat. No. 6,399,151 to Zaretsky issued on Jun. 4, 2002). The corona electrode moves over the chargeable material 34 as the mail chute 16 is rotated.

Returning to FIGS. 4a and 4b, charging means 32 are activated when mail chute 16 is opened and/or closed. (The mail chute 16 is in an open position when the input end 12 is aligned with the opening 19.) The charging means 32 are preferably activated when mail chute 16 is closed, as illustrated in FIGS. 5a, 5b. The charging means 32 statically charge the surface of the chargeable material 34. The nature and composition of the chargeable material 34 depend on the embodiment of the charging means.

Referring to FIG. 4b, in the embodiment shown in FIG. 5c, in which charging means 32, includes electrodes 74, 76 and the voltage source 44, the voltage source 44, preferably DC, provides energy to power the charging means 32. Voltage source 44 can include a DC source, an AC source and power supply, or a photovoltaic array (a solar powered voltage source). Charging means 32 are activated when mail chute 16 is opened and/or closed. FIG. 4b also applies to the embodiment similar to that of U.S. Pat. No. 3,935,517.

Figure 6:
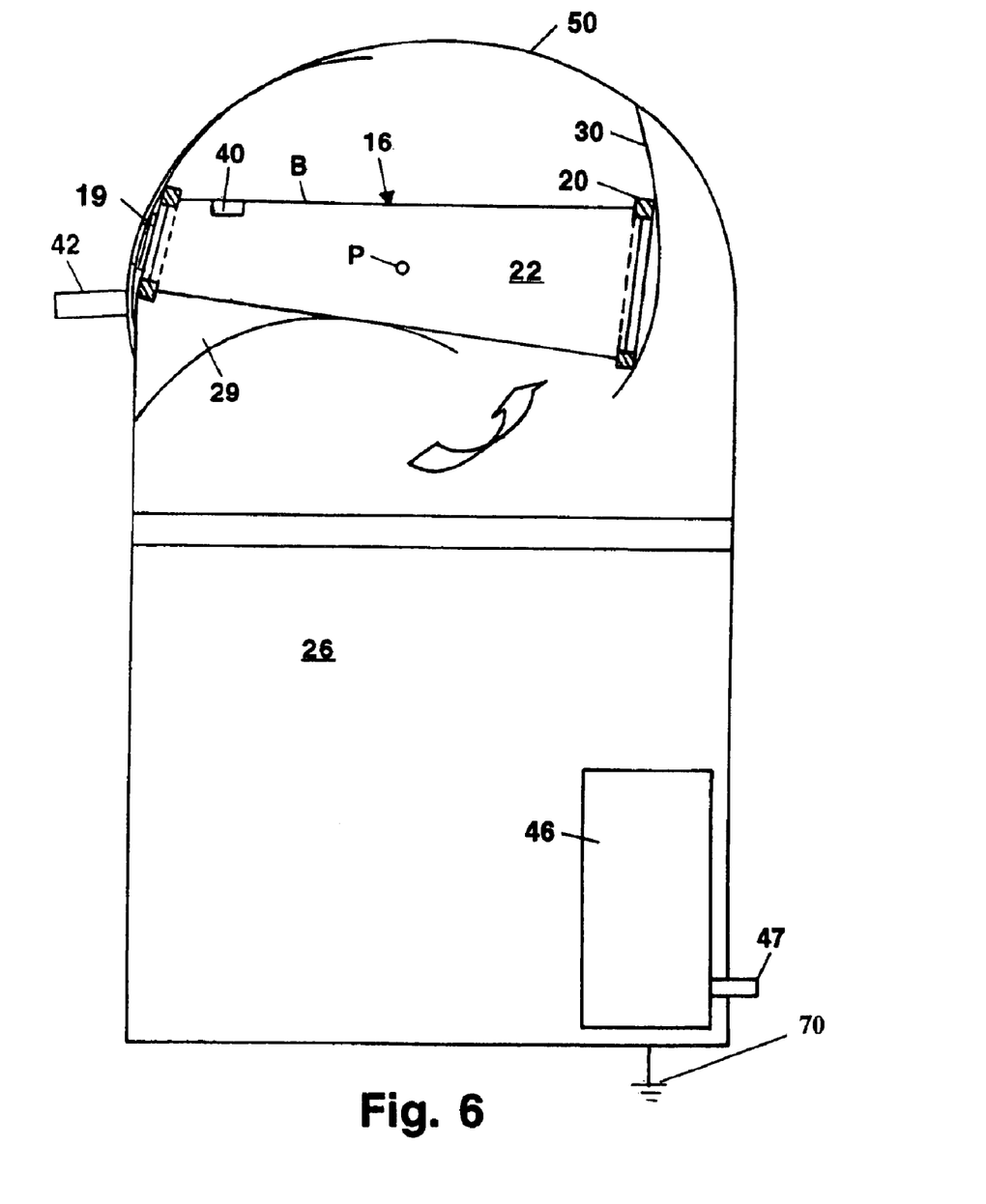
FIG. 6 is a sectional side view of a conventional collection box adapted with a dehumidifier to maintain dry air in the collection box.
Figure 7:
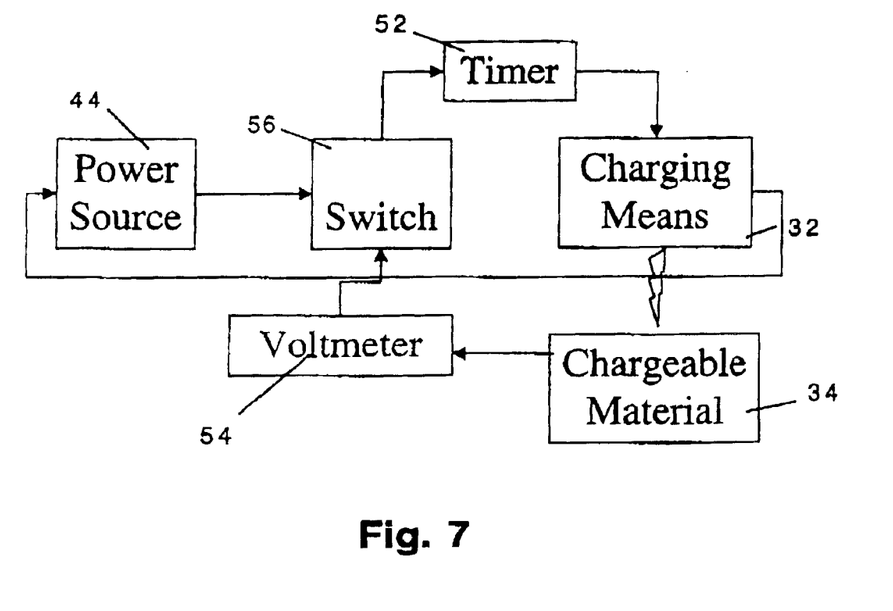
FIG. 7 is a block diagram of another embodiment of the electrical circuit of the present invention.

As illustrated in FIG. 6, an alternative embodiment includes a dehumidifier 46, having a drain tube 47, incorporated into the collection box 50 to dry the air for a higher charge and greater retention of the static charge on the conductive material 34. The dehumidifier 46 reduces humidity that impacts surface leakage and, therefore, the amount of charge on a surface.

Now returning to FIGS. 5a, 5b, 5c, the materials comprising sector section 62 and 64, materials comprising sector section 66 and 68, and electrodes 74, 76 are embodiments of the chargeable material 34. Charged pathogen agents are drawn to the oppositely charged chargeable material 34. Therefore, pathogen particles that are airborne and dispersed on local surfaces, such as mail pieces 38 and mail chute interior walls 48, will be attracted to chargeable material 34 and substantially removed from the mail chute passage 22. Chargeable material 34 can be periodically replaced by hazardous material specialists for appropriate disposal. The collection box 50 is grounded to assure mail carriers are not shocked during performing their duties of picking up the mail.

The chargeable material 34 can be placed in any location within the mail chute 16 or near the inlet mail deposit opening 12. Now returning to FIG. 3, one embodiment of the present invention, such as that shown in FIG. 5a, places the charging means 32 and chargeable material 34 about the pivot point P of the mail chute 16. A mail piece 38 enters the inlet mail deposit opening 12 and passes the chargeable material 34 such that charged pathogen particles on the mail piece 38 or mail chute interior walls 48 are drawn to the oppositely charged chargeable material 34. The attractive properties or strength of the chargeable material 34 can be adjusted by design in the embodiments of FIGS. 5a, 5b, or by increasing the intensity of the voltage source 44 to accommodate the placement of the chargeable material 34.

Now returning to FIGS. 4a, 4b, an alternative embodiment can include a timer 52 that will deactivate the charging means 32 after a predetermined period. In the embodiments of FIGS. 5a and 5b, deactivation includes grounding sector section 62 and 64 or grounding sector section 66 and 68. In the embodiment of FIG. 5c and similar embodiments, deactivation includes disabling the connection between the voltage source 44 and electrodes 74, 76. Alternatively, referring to FIG. 4b, the timer 52 can be programmed to periodically turn on and off to clear the air in the mail chute 16 and reduce the possible plume of airborne pathogen particles that may be released if the collection box 50 had not been used for an extended period.

Yet a further alternative embodiment, related to the embodiment shown in FIG. 5c or the embodiment similar to that of U.S. Pat. No. 3,935,517 or the corona charging embodiment, includes a voltmeter 54 connected to the chargeable material 34, as illustrated in FIG. 7. The voltmeter 54 monitors the static charge of the chargeable material 34. (Measuring charge by measuring voltage is an indirect measurement. It should be noted that, if the capacitance is known, the charge equals capacitance times the voltage.) When the charge drops below a low threshold predetermined level the voltage source 44 is switched on, via switch 56, to energize the charging means 32 and recharge the chargeable material 34 to a higher level than the predetermined threshold level. It should be noted that switch 56 could be the same switch as door switch 40. The timer 52 will deactivate the charging means 32 after a predetermined period. The periodic recharging of the conductive material 34 prevents pathogen particles from being released from the conductive material 34 and freely floating within the mail chute passage 22 to eventually settle on the mail chute walls 48.

It should be noted that other embodiments in which the charging means 32 include triboelectric means are possible in addition to those disclosed in FIGS. 5*a*, 5*b*. For example, the chargeable materials 34 could be placed near the inlet opening 12 of mail chute 16. When the mail chute 16 is rotated, the appropriately selected chargeable materials 34 will move out of contact and become charged.

It should noted that although in the above disclosed embodiments, grounding and grounding means have been disclosed without details, conventional grounding methods and grounding means can be utilized. Exemplary grounding means are grounding straps, connections to a ground conductor, connections to a system ground. Exemplary grounding methods include, but are not limited to, connecting to a system ground or a ground connector.

It should also be noted that, in the embodiment in which the mail chute 16 is operably connected to the mail inlet cover 42, the operable connection between the mail chute 16 and the mail inlet cover 42 can be established by conventional mechanical or electromechanical means.

Although the invention has been described with respect to various embodiments, it should be realized this invention is also capable of a wide variety of further and other embodiments within the spirit and scope of the present invention.

What is claimed is:

1. A collection box comprising:

a container having an outer surface, an inner chamber and an opening located in a first preselected portion of said container;

a chute element moveably mounted within said inner chamber, said chute element having an input end and an output end;

said input end capable of receiving items through said opening when aligned with said opening;

said output end capable of permitting the items to pass therethrough into a preselected portion of said inner chamber, said chute element permitting transport of the items from said input end to said output end when said chute element is moved into a preselected position; and sealing means for sealing said input end of said chute element with respect to said opening and for sealing said output end of said chute element based upon the movement of said chute element;

whereby, upon movement of said chute element to a position when said input end is aligned with said opening, said output end is sealed from said inner chamber, and upon movement of said chute element to a position when said output end is no longer sealed, said input end is sealed from said opening.

2. The collection box as defined in claim 1 wherein said chute element is pivotally mounted within said container for rotational movement with respect to said inner chamber;

whereby said input end is capable, in one angular position of rotation, of receiving the items from said opening, and said output end is capable, in another angular position of rotation, of delivering items into said second preselected portion of said container.

3. The collection box of claim 1 further comprising:

means for covering said opening, said means operably connected to the chute element.

4. The collection box of claim 1 further comprising:

means for electrically charging a portion of the chute element;

means for electrically grounding the container; and, means for electrically grounding the preselected portion of the inner chamber.

5. The collection box of claim 4 further comprising:

means for dehumidifying the inner chamber.

6. The collection box of claim 4 further comprising:

means for measuring an applied voltage utilized for charging the portion of the chute element; and means for restoring said applied voltage to a previous level.

7. The collection box of claim 4 further comprising:

a timer and switch mechanism for deactivating said electrically charging means.

8. The collection box of claim 4 further comprising:

means for energizing said charging means upon movement of the chute element into a preselected position.

9. The collection box of claim 4 further comprising:

means for energizing said charging means upon substantial alignment of said open end with said opening.

10. The collection box of claim 4 wherein the charging means comprise triboelectric charging means.

11. The collection box of claim 4 wherein the charging means comprise a voltage source and two electrodes.

12. The collection box of claim 11 wherein the voltage source is selected from the group consisting of a DC source, an AC source, a photovoltaic source.

13. A method for isolating items in a collection box comprising the steps of:

aligning an input end of a chute element with an opening, said opening located in a preselected portion of a container in a collection box;

sealing an output end of the chute element when the input end is aligned with the opening;

receiving, in the chute element, at least one item introduced through said opening;

moving the chute element into a preselected position;

sealing, after moving the chute element into a preselected position, the input end;

unsealing, after moving the chute element into a preselected position, the output end;

whereby the item is deposited within the collection box.

14. The method of claim 13 further comprising the step of:

electrically charging an inner surface area in said chute element.

15. The method of claim 14 wherein the step of electrically charging said inner surface area occurs upon moving the chute element into a preselected position.

16. The method of claim 14 wherein the step of electrically charging said inner surface area occurs upon aligning said input end with said opening.

17. The method of claim 14 further comprising the step of:

dehumidifying an ambient atmosphere inside said inner chamber.

18. The method of claim 14 further comprising the steps of:

measuring an applied voltage utilized for charging the inner surface area; and restoring said applied voltage to a previous level.

19. The method of claim 14 further comprising the step of:

deactivating said electrical charging after a given time period.

20. The method of claim 14 wherein the step of electrically charging said inner surface area further comprises the steps of:

bringing two materials into contact, said materials being selected from opposite ends of a triboelectric series;

placing said materials out of contact;

whereby said two materials acquire a charge upon being brought out of contact.

21. The method of claim 14 wherein the step of electrically charging said inner surface area further comprises the step of:

applying a voltage between two electrodes, one of said two electrodes including said inner surface area.

22. The method of claim 13 further comprising the step of:

unsealing the input end of the chute element when the input end is aligned with the opening, if the input end was previously sealed.

23. A collection box comprising:

a container having an outer surface, an inner chamber and an opening located in a first preselected portion of said container;

said opening being capable of allowing physical access into a preselected portion of said inner chamber by means of a chute element;

said chute element having an input end and an output end;

said input end capable of receiving items through said opening;

said output end capable of permitting the items to pass therethrough into said preselected portion of said inner chamber;

means for electrically charging a portion of the chute element;

means for electrically grounding the container;

whereby, upon electrically charging of said portion of said element, said charged portion is capable of collecting charged airborne particles.

24. The collection box of claim 23 further comprising:

means for covering said opening, said means operably connected to charging means.

25. The collection box of claim 23 wherein said input end is aligned with said opening.

26. The collection box of claim 23 wherein said output end is aligned with said opening.

27. The collection box of claim 23 further comprising:

means for electrically grounding the preselected portion of the inner chamber.

28. The collection box of claim 23 further comprising:

means for dehumidifying the inner chamber.

29. The collection box of claim 23 further comprising:

means for measuring an applied voltage utilized for charging the portion of the chute element; and means for restoring said applied voltage to a previous level.

30. The collection box of claim 23 further comprising:

a timer and switch mechanism for deactivating said electrically charging means.

31. The collection box of claim 23 further comprising:

means for energizing said charging means upon opening said covering means.

32. The collection box of claim 23 further comprising:

means for energizing said charging means upon closing said covering means.

33. The collection box of claim 1 wherein the charging means comprise triboelectric charging means.

34. The collection box of claim 23 wherein the charging means comprise a voltage source and two electrodes.

35. The collection box of claim 34 wherein the voltage source is selected from the group consisting of a DC source, an AC source, a photovoltaic source.

* * * * *

UNITED STATES PATENT AND TRADEMARK OFFICE
CERTIFICATE OF CORRECTION

PATENT NO. : 6,918,534 B2
DATED : July 19, 2005
INVENTOR(S) : Fitzgibbons et al.

It is certified that error appears in the above-identified patent and that said Letters Patent is hereby corrected as shown below:

Column 10,
Line 44, "1" should read -- 23 --.

Signed and Sealed this

Twenty-seventh Day of September, 2005

JON W. DUDAS
*Director of the United States Patent and Trademark Office*